United States Patent
Lindemann et al.

(10) Patent No.: US 10,731,202 B2
(45) Date of Patent: Aug. 4, 2020

(54) CHROMATIN ACTIVITY PRECIPITATION METHOD AND SYSTEM

(71) Applicant: Battelle Memorial Institute, Richland, WA (US)

(72) Inventors: Stephen R. Lindemann, Lafayette, IN (US); Aaron T. Wright, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 286 days.

(21) Appl. No.: 15/527,996

(22) PCT Filed: Nov. 11, 2015

(86) PCT No.: PCT/US2015/060171
§ 371 (c)(1),
(2) Date: May 18, 2017

(87) PCT Pub. No.: WO2016/085659
PCT Pub. Date: Jun. 2, 2016

(65) Prior Publication Data
US 2017/0342469 A1 Nov. 30, 2017

Related U.S. Application Data

(60) Provisional application No. 62/083,705, filed on Nov. 24, 2014.

(51) Int. Cl.
| | |
|---|---|
| C12Q 1/6809 | (2018.01) |
| C12N 15/10 | (2006.01) |
| C12Q 1/6816 | (2018.01) |
| C12Q 1/6869 | (2018.01) |

(52) U.S. Cl.
CPC .......... C12Q 1/6809 (2013.01); C12N 15/10 (2013.01); C12Q 1/6816 (2013.01); C12Q 1/6869 (2013.01); C12Q 2523/101 (2013.01); C12Q 2523/319 (2013.01)

(58) Field of Classification Search
CPC .... C12N 15/10; C12Q 1/6809; C12Q 1/6816; C12Q 1/6869; C12Q 2523/101; C12Q 2523/319
See application file for complete search history.

(56) References Cited

FOREIGN PATENT DOCUMENTS

WO 2006/116736 A2 11/2006

OTHER PUBLICATIONS

Cisar et al. (J. Amer. Chem. Soc., 2012, 134:10385-10388) (Year: 2012).*
Sibbersen et al. (Chem. Commun., 2014, 50, 12098-12100) (Year: 2014).*
Koehler (Cur. Op. Chem. Biol., 2010, 14:331-340) (Year: 2010).*
(Continued)

Primary Examiner — Jeremy C Flinders
(74) Attorney, Agent, or Firm — Derek H. Maughan

(57) ABSTRACT

Methods and systems for identifying binding sites in macromolecules using small molecule mimics of naturally occurring molecules is disclosed. A reactive probe is provided that mimics small molecule cofactors. A target macromolecule is irreversibly bound to the probe in vivo to selectively pull down or precipitate probe-bound macromolecules. The macromolecules may be, but are not limited to, DNA, RNA, and proteins.

14 Claims, 4 Drawing Sheets

(56) References Cited

OTHER PUBLICATIONS

International Search Report/Written Opinion for International Application No. PCT/US2015/060171, International Filing Date Nov. 11, 2015, dated Jan. 29, 2016.
Ansong, C., et al., Identification of Widespread Adenosine Nucleotide Binding in Mycobacterium tuberculosis, Chemistry and Biology, 20, 1, Jan. 24, 2013.
Evans, M. J., et al., Mechanism-Based Profiling of Enzyme Families, Chemical Reviews, 106, 8, Jul. 15, 2006.

* cited by examiner

CHROMATIN ACTIVITY PRECIPITATION METHOD AND SYSTEM

CROSS-REFERENCE TO RELATED APPLICATIONS

This application is a 35 U.S.C. § 371 of International Application Serial No. PCT/US2015/060171 filed Nov. 11, 2015, which claims priority from U.S. Provisional Application Ser. No. 62/083,705 filed Nov. 24, 2014 titled "CHROMATIN ACTIVITY PRECIPITATION METHOD AND SYSTEM", which is incorporated in its entirety herein by reference.

STATEMENT REGARDING FEDERALLY SPONSORED RESEARCH OR DEVELOPMENT

This invention was made with Government support under Contract DE-AC0576RL01830 awarded by the U.S. Department of Energy. The Government has certain rights in the invention.

TECHNICAL FIELD

This invention relates to chromatin precipitation. More specifically, this invention relates to chromatin precipitation by using small molecule mimics of naturally occurring molecules.

BACKGROUND

Metagenome analysis routinely uncovers a significant diversity of microorganisms with apparently-redundant functions in environmental and host-associated communities, bringing into question how such diversity is maintained as organisms compete for resources. The functional role of an organism in a community is routinely inferred by prediction of its genome-encoded metabolic functionality, which is highly sensitive to the quality and specificity of gene annotation but blind to how those genes are expressed. Global approaches can quantitatively identify changes in gene regulation with respect to changes in conditions, but do not shed light on the regulatory proteins responsible for their activation or repression nor the specific environmental signals they recognize.

Although global gene expression analyses (e.g., transcriptomics, proteomics) frequently implicates coordination of gene expression that is regulated by environmental conditions, identifying the specific mechanisms by which genes are regulated has been dependent on isolation of specific target microbes and genetic manipulation of cultured strains. Global approaches can quantitatively identify changes in gene regulation with respect to changes in conditions, but do not shed light on the regulatory proteins responsible for their activation or repression nor the specific environmental signals they recognize. Consequently, changes in expression of any given gene may stem from cascading, compensatory changes in gene regulation that are second- or third-order to the environmental stimulus. Validation of a putative regulatory protein initially identified using a global approach traditionally requires deletion of a putative regulator, examination of the effect on gene expression under various conditions, and DNA footprinting and/or gel-shift assays to identify the regulator's binding sites on the bacterial chromosome. This process has been dramatically quickened through chromatin immunoprecipitation (ChIP) hybridization or sequencing. In ChIP, antibodies against a known regulatory protein are used to precipitate DNA bound to the regulator, which is then sequenced to identify the protein's binding sites. Traditional ChIP-seq requires a priori knowledge of which regulators are important for processes of interest. Because ChIP is dependent upon antibody recognition of the target regulator, it entails either an arduous process of cloning the gene encoding a regulatory protein of interest, purifying the native regulatory protein, and generating antibodies or appending an epitope tag to a gene on the chromosome of a genetically-tractable host organism. These approaches are species-specific and technically challenging; consequently, ChIP-seq is typically employed in only well-studied and tractable organisms. Additionally, ChIP typically does not provide information regarding the signal to which a given regulator is responding as it binds DNA. As natural communities frequently contain diverse organisms that have not yet been cultivated, much less made genetically tractable, ChIP cannot be effectively used to dissect out the mechanisms by which multiple members respond to the identical environmental stimulus. Furthermore, for poorly-characterized axenic isolates, the amount of prior information and investment required to successfully perform ChIP against a putative regulator makes this approach highly investment-intensive and technically uncertain.

What is needed is an approach to gene regulation that is responsive to a specific small-molecule probe, is generalizable across species, and requires no prior knowledge and only modest investment. Such an approach would be applicable to examining gene regulatory mechanisms in both prokaryotic and eukaryotic organisms that respond to small molecule signals.

SUMMARY

The present invention is directed to methods and systems for chromatin activity precipitation. In one embodiment of the present invention, a method of identifying binding sites in macromolecules using small molecule mimics of naturally occurring molecules is disclosed. The method includes providing a reactive probe that mimics small molecule cofactors, and irreversibly binding a target macromolecule to the probe in vivo to selectively pull down or precipitate probe-bound macromolecules.

The macromolecules may be, but are not limited to, deoxyribonucleic acid (DNA), ribonucleic acid (RNA), and proteins. The proteins may be, but are not limited to, transcription factors.

In one embodiment, the probe includes a photo-crosslinker, and an alkyne or an azide. The photo-crosslinker is, but not limited to, diazirine or benzophenone.

The method may further include exposing the photo-crosslinker to UV light wherein the target macromolecule interacting with the probe is covalently attached to the probe, forming a probe-bound macromolecular complex. The macromolecular complex may be cross-linked to the target macromolecule using aldehyde, formaldehyde, or paraformaldehyde.

The method may also include enriching the probe-bound macromolecular complex by adding an enrichment group or a detection group to the alkyne or azide portion of the probe using copper (I) cycloaddition. In another embodiment, the method may include performing click chemistry on azide or alkyne-coated beads.

In one embodiment, the enrichment group is biotin, and the detection group is at least one of the following: fluorophores, nanoparticles, and quantum dots.

In one embodiment, the macromolecular complex is removed from any unbound macromolecules by affinity purification through binding to monomeric avidin or streptavidin resin, wherein fractions from the monomeric avidin-bound, streptavidin-bound, and/or the unbound macromolecules are harvested for analysis.

Post-elution, the cross-linking in the avidin-bound or streptavidin-bound fractions may be reversed by heat treatment from which fractions of the macromolecules will be separated.

In one embodiment, the macromolecule irreversibly binding the probe is identified by LC-MS, DNA or RNA sequencing, or both, which yields an entire set of macromolecules binding the probe.

In another embodiment of the present invention, a method of identifying binding sites in macromolecules using small molecule mimics of naturally occurring molecules is disclosed. The method includes providing a reactive probe that mimics small molecule cofactors, and irreversibly binding a target RNA to the probe in vivo to selectively pull down or precipitate macromolecules.

In one embodiment, the method may further include exposing the photo-crosslinker to UV light wherein the target RNA interacting with the probe is covalently attached to the probe, forming a probe-bound binary complex.

The method may also include, in one embodiment, enriching the probe-bound RNA complex by adding an enrichment group or a detection group to the alkyne or azide portion of the probe using copper (I) catalyzed or strain-promoted cycloaddition.

In one embodiment, the RNA irreversibly binding the probe is reverse transcribed and sequenced, which yields an entire set of RNA macromolecules binding the probe.

In another embodiment of the present invention, a method of identifying binding sites in macromolecules using small molecule mimics of naturally occurring molecules is disclosed. The method includes providing a reactive probe that mimics small molecule cofactors, and irreversibly binding a target protein to the probe in vivo to selectively pull down or precipitate probe-bound transcription factors and target nucleic acids. The nucleic acids are DNA or RNA.

The method may further comprise exposing the photo-crosslinker to UV light wherein the target protein interacting with the probe is covalently attached to the probe, forming a probe-bound macromolecular complex, wherein the macromolecular complex is cross-linked to the target nucleic acids using aldehyde, formaldehyde, or paraformaldehyde.

The method may also include enriching the probe-bound macromolecular complex by adding an enrichment group or a detection group to the alkyne or azide portion of the probe using copper (I) cycloaddition, wherein the enrichment group is biotin or avidin, and the detection group is at least one of the following: fluorophores, nanoparticles, and quantum dots.

In one embodiment, the protein irreversibly binding the probe is identified by LC-MS, DNA or RNA sequencing, or both, which yields an entire set of macromolecules binding the probe.

DETAILED DESCRIPTION OF THE PREFERRED EMBODIMENTS

Figure 1:
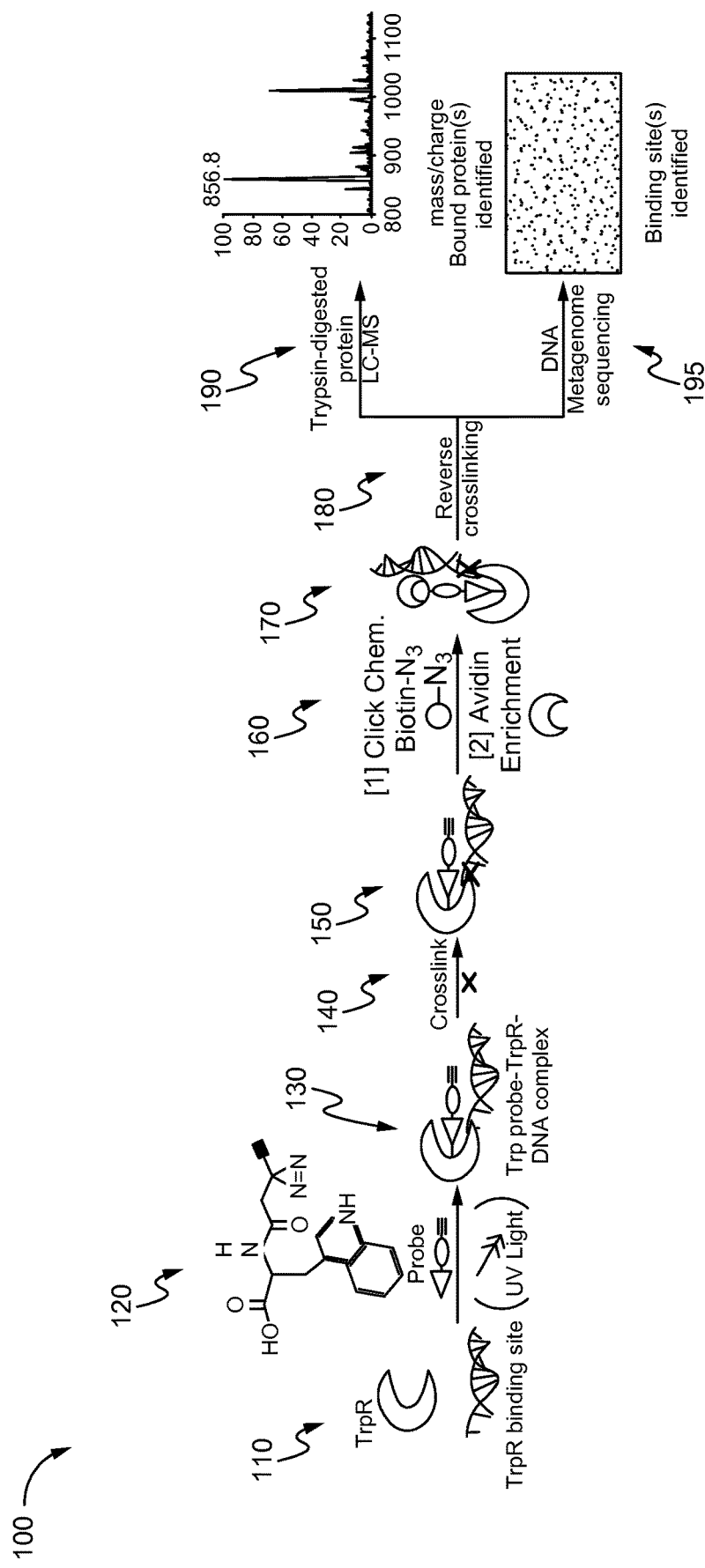
FIG. 1 is a schematic flow diagram for a method of identifying binding sites in macromolecules using small molecule mimics of naturally occurring molecules, in accordance with one embodiment of the present invention.

The following description includes the preferred best mode of embodiments of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Disclosed are methods and systems elucidating macromolecules, such as proteins, DNA, and RNA and their binding sites, based upon binding of regulators by small molecule mimics. The methods of the present invention can be used to analyze metabolite regulated proteins and promoters in microbial prokaryotic organisms, eukaryotic organisms, and in microbial communities or higher organisms. The present invention can be used to identify mechanisms of gene regulation across multiple organisms within a community. The present invention can also identify how genes are regulated in a microbial community in response to environmental stimuli. Using the methods of the present invention, macromolecules and their corresponding binding sites are able to be determined. The macromolecules include, but are not limited to, DNA, RNA, carbohydrates, proteins, peptides, using probe molecules mimicking amino acids, carbohydrates, and/or vitamins or other cofactors.

In one embodiment of the present invention, activity-based probes are used to mimic small molecules that are cofactors, binding irreversibly to a target macromolecule. In this way, the probe-bound macromolecule or macromolecules can be pulled down or precipitated. Synthesized probes are used based upon the structures of the target macromolecules known to be important in cellular physiology. The probes are designed to mimic the native molecule.

In one embodiment, the probes are coupled to a photo-crosslinker and an alkyne or azide cycloaddition. The photo-crosslinker, which may be but is not limited to diazirine or benzophenone, can be excited by UV light, which binds irreversibly to the target macromolecule. The macromolecular complex can be cross-linked using aldehyde, formaldehyde, or paraformaldehyde, and may include at least one of the following: biotin, GST tags, or HA tags. The macromolecular complex may be enriched by adding an enrichment group or a detection group to the alkyne or azide portion of the probe using copper (I) catalyzed or strain-promoted cycloaddition, and/or click chemistry may be performed on azide or alkyne-coated beads. The macromolecular complex is removed from any unbound macromolecules by affinity purification through binding to avidin or streptavidin. Fractions from the avidin-bound, streptavidin-bound, and/or the unbound macromolecules are harvested for analysis. Post-elution, the cross-linking in the avidin-bound or streptavidin-bound fractions will be reversed by heat treatment from which fractions of the macromolecules will be separated. After enrichment and purification, the macromolecule irreversibly binding the probe is identified by LC-MS, DNA or RNA sequencing, or both, which yields an entire set of macromolecules binding the probe.

FIG. 1 shows a schematic flow diagram 100 for a method of identifying binding sites in macromolecules using small molecule mimics of naturally occurring molecules, in accordance with one embodiment of the present invention. The embodiment shown in FIG. 1 is specific for a probe-protein-DNA complex using tryptophan-mimicking probes as an example. At 110, the tryptophan repressor protein (TrpR) is used to identify TrpR binding sites which will bind the probe and DNA. The DNA includes a TrpR binding site. The structure of the synthesized activity-based TrpR probe is shown at 120. The probe includes a reactive group, a linker (photo-crosslinker), and an alkyne or azide. The photo-crosslinker is exposed to UV light, forming a probe-bound complex, as shown at 130, wherein the TrpR protein is covalently attached to the probe. At 140, the TrpR-probe complex is cross-linked to the DNA protein using aldehyde, formaldehyde, or paraformaldehyde, forming a strong bond at 150. For enrichment of the probe-bound protein and the DNA, at 160, a copper (I)-catalyzed cycloaddition reaction (click chemistry) is used to attach an enrichment group or detection group to the alkyne portion of the probe for subsequent enrichment of probed proteins and bound DNA, as shown at 170. The enrichment group is, but not limited to, biotin or avidin, and the detection group is but not limited to fluorophores, nanoparticles, or quantum dots. At 180, post-elution, the crosslinking in the avidin-bound fraction is reversed by heat treatment, from which the DNA and protein fractions are separated. Proteins irreversibly binding these probes are purified for proteomic analysis by LC-MS at 190. At 195, DNA fractions (probe-protein-bound and unbound) are sequenced to determine which fragments were captured Both captured and uncaptured DNA fragments are sequenced in parallel to detect which fragments are substantially enriched or depleted. Binding sites for probe-bound regulators should be enriched in the biotin/avidin-captured fraction and depleted within the uncaptured fraction.

EXAMPLES

The following examples are offered to illustrate but not limit the invention.

Example 1

B-12 Probe for Direct RNA Binding

Figure 2:
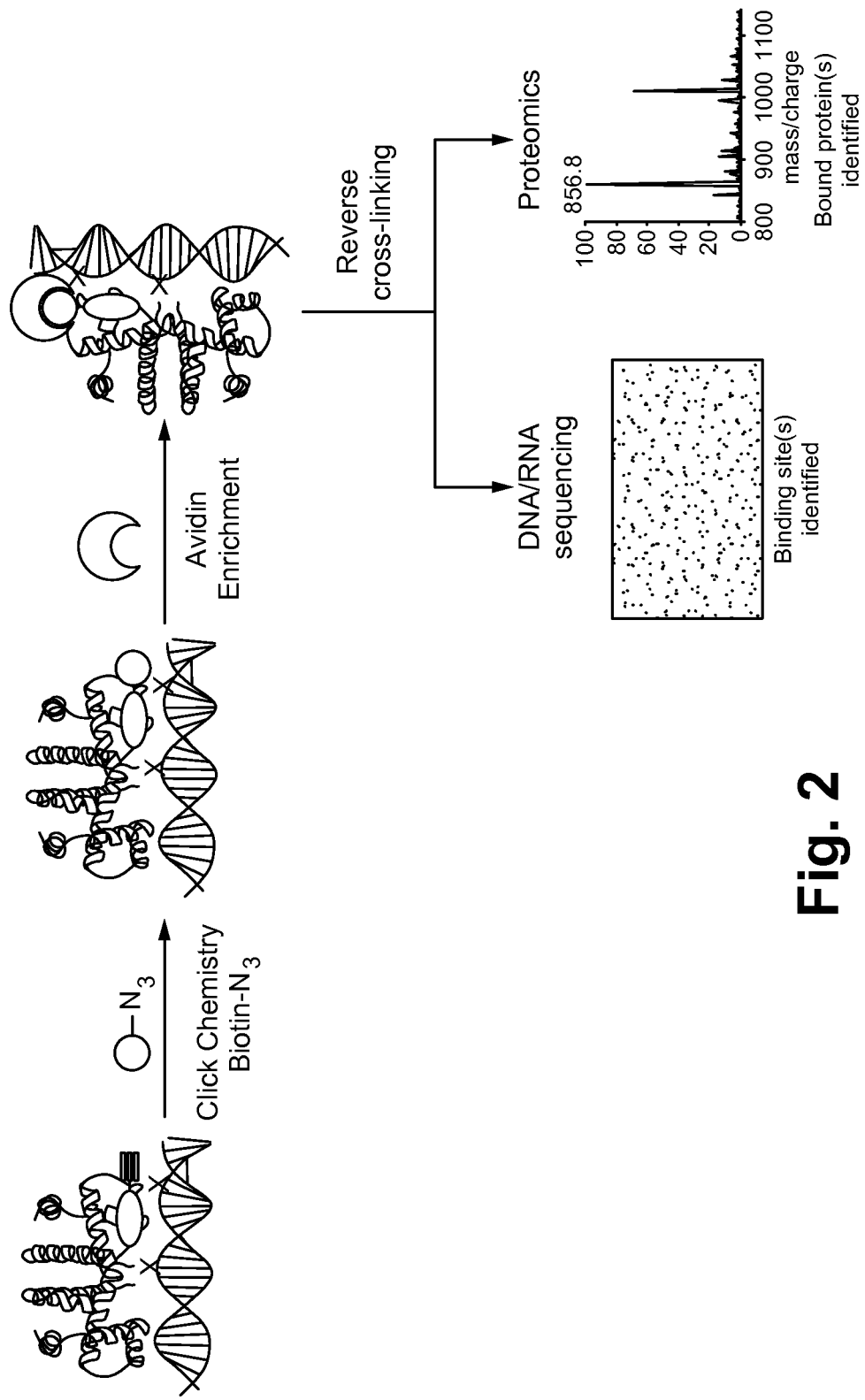
FIG. 2 is a schematic flow diagram for a method of identifying binding sites in macromolecules using small molecule mimics of naturally occurring molecules, in accordance with one embodiment of the present invention.

FIG. 2 is a schematic flow diagram for a method of identifying binding sites in macromolecules using small molecule mimics of naturally occurring molecules, in accordance with one embodiment of the present invention. The embodiment shown in FIG. 2 is specific for a probe-RNA complex, but the flow path has many of the same features as the method illustrated in FIG. 1.

In FIG. 2, a B12-probe was validated for RNA binding. Using copper (I) cycloaddition, an enrichment moiety, biotin, is added to the probe-bound RNA. Magnetic beads coated with avidin can then be used to selectively recruit cross-linked probe-RNA-complexes. Paraformaldehyde cross-linking is then reversed, bound nucleic acids are then examined using next-generation sequencing and, in cases of probe-protein-nucleic acid complexes, protein regulators can also be assayed using LC-MS based proteomic approaches. The method described in FIG. 2 can identify regulatory mechanisms and their binding sites.

Figure 3A:
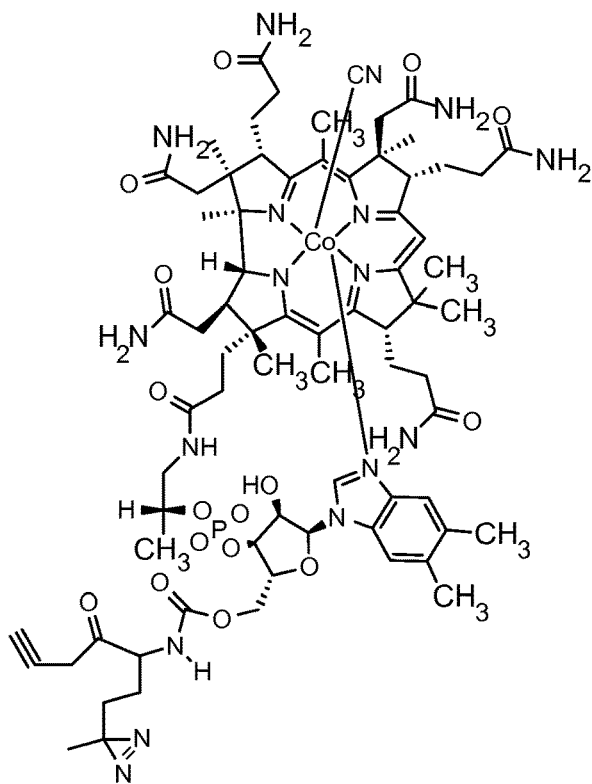
FIG. 3A is a schematic diagram of a Vitamin B12 structure used for validation for RNA binding.

FIG. 3A is a schematic diagram of a Vitamin B12 structure used as the probe in FIG. 2 for validation of RNA binding. A diazirine photo-crosslinker and an alkyne handle for copper (I) cycloaddition (click chemistry) are added on leucine attached via an amide bond to the ribose of the adenosyl residue.

Figure 3B:
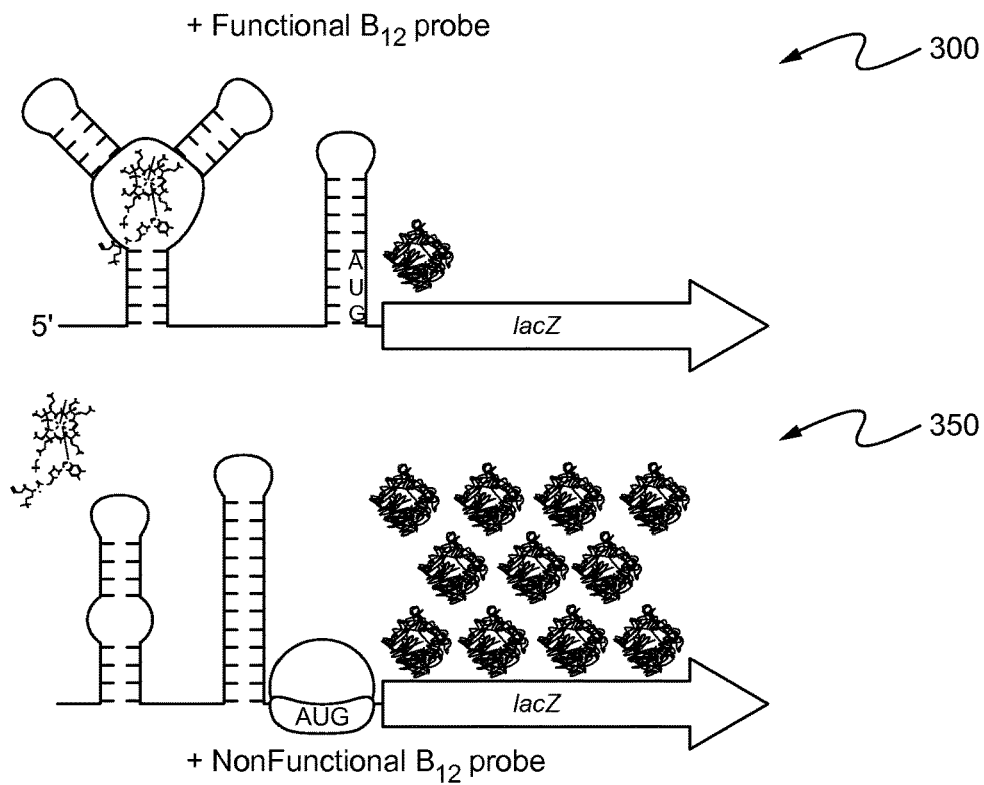
FIG. 3B is a schematic diagram of a Miller assay for high-throughput evaluation of probe molecule activity, using a functional B12 probe and a non-functional B12 probe.

FIG. 3B is a schematic diagram of a Miller assay for high-throughput evaluation of probe molecule activity, using a functional B12 probe and a non-functional B12 probe of FIG. 3A. The $E.$ $coil$ B12 riboswitch was cloned upstream of a gene encoding beta-galactosidase, which can be spectrophotometrically measured using cleavage of yellow o-nitrophenol from o-nitrophenol-b-galactosidase.

Figure 3C:
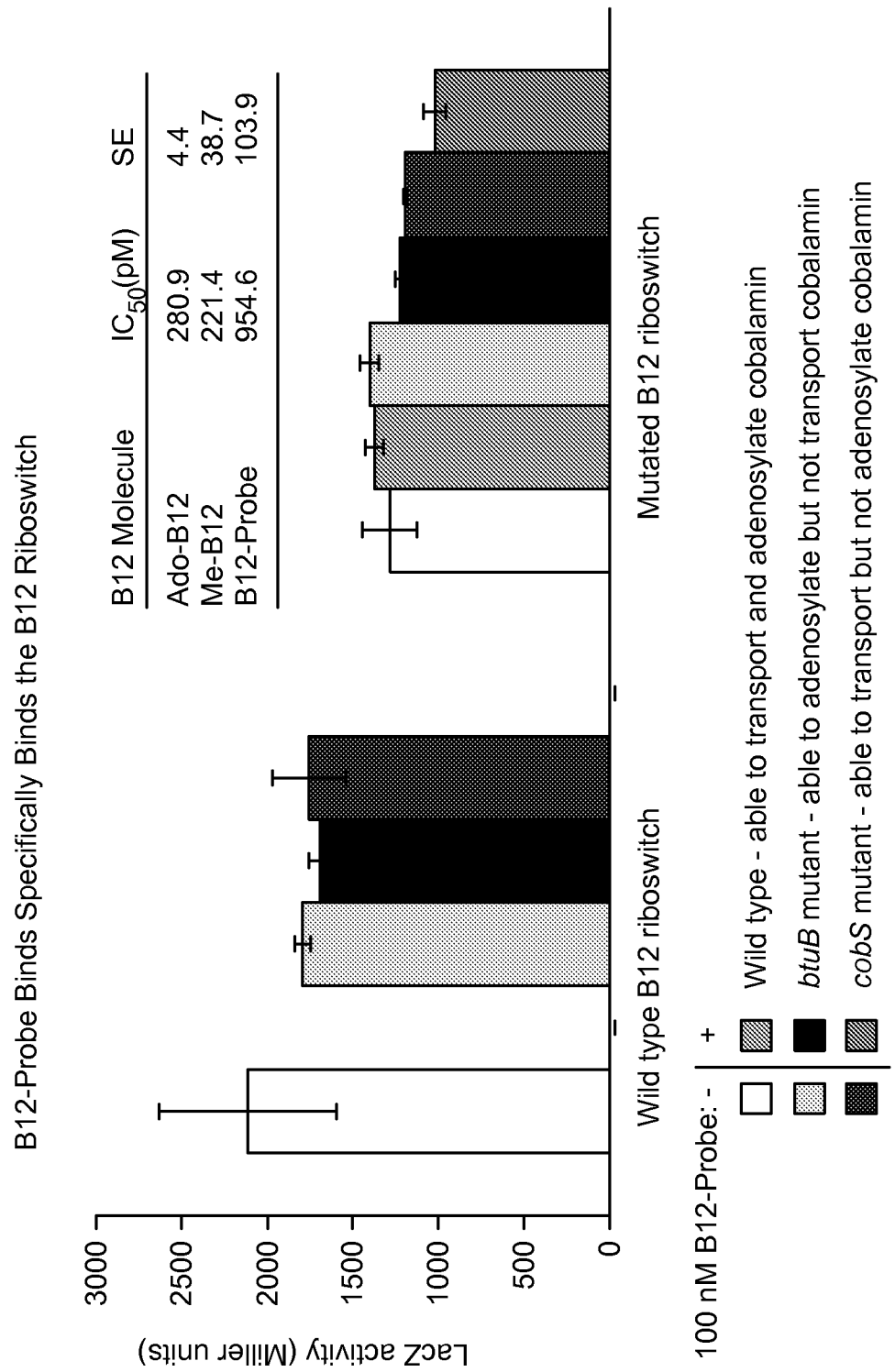
FIG. 3C shows the results for the assay described in FIG. 3B, which shows the B12 probe hound to the B12 Riboswitch.

FIG. 3C shows the results for the assay described in FIG. 3B, which shows the B12 probe bound to the B12 Riboswitch. The B12-probe was validated for RNA binding using its affinity for the B12 riboswitch in the Miller Assay described in FIG. 3B. Similar to normal B12, repression via. B12-probe was specific for the riboswitch and dependent upon the B12 transporter. B12-probe represses with similar affinity as active forms of vitamin B12.

Example 2

TrpR-Mimic Probes in $E.$ $coli$ to Identify Known Binding Site for TrpR.

The following is a prophetic example to show repression of tryptophan synthesis genes by tryptophan repressor, TrpR. Using our previously-synthesized Trp activity-based probe, one embodiment of the present invention, as shown in the flow path of FIG. 1, is performed on wild-type $E.$ $coli$ MG1655 and well-known trpR mutants (e.g., CSH22 and CY15682) as negative controls for TrpR binding. These strains will be grown in Trp-free M9 minimal medium with glucose as the sole carbon source to mid-log phase ($OD_{600}$~0.5 Abs) and labeled with micromolar quantities of Trp probe. Cultures will be harvested following a short incubation as described above in varying concentrations of Trp probe. Our results should identify all Trp-binding proteins in $E.$ $coil$ inclusive of TrpR, detect all of the known binding sites for TrpR on the $E.$ $coli$ chromosome, and greatly enrich TrpR from the chromosome as the sole protein both binding the probe and DNA. From these data, DNA binding affinities for Trp probe-TrpR complexes will be calculated and compared to well-known affinities for the Trp-TrpR complex to determine if and to what degree the probe modifications affect DNA binding. This proof-of-principle experiment may also validate the binding sites for TrpR detected in ChIP-chip but not yet empirically proven by gel-shift assays. Mutants in trpR should exhibit probe binding to all proteins detected in wild-type MG1655 except TrpR itself and display no binding to DNA, thus serving as a control for probe specificity.

Example 3

Identity Heretofore-Unknown Vitamin-Binding Transcription Factors in Axenic Microbes and Mixed Cultures to Demonstrate the Present Invention in Microbial Communities.

The following is a prophetic example to elucidate unknown transcription factor regulons responsive to vitamins. It is known that members of the CarH family of transcriptional regulators bind vitamin B12 to exert their regulatory function, but members of this family are difficult to predict from gene sequences. For this approach, we use vitamin probes previously synthesized by our group to identify vitamin regulons in Halomonas species which are predicted to possess both a B12-binding riboswitch and a CarH-like B12-binding transcription factor. Work is ongoing to experimentally identify both the riboswitch and the transcription factor and its binding sites, work that would be synergistic with a global approach via the methods of the present invention. Consequently, methods of the present invention provide a potential means to detect the B12-binding regulator in these species, assign it to the predicted B12 regulon, and validate its binding site.

Methods of the present invention will be performed in these Hamonas species grown with minimal vitamin supplementation to provide a global, prediction-insensitive approach to identifying vitamin-binding regulators of vitamin synthesis in tandem with experiments to validate these regulator/binding, site pairs. Once the methods have been empirically determined to identify vitamin regulator/target motif pairs in axenic Halomonas species, identical analyses in biofilm cultures of unicyanobacterial consortia, which include the target species above, will be performed to evaluate the suitability of the methods disclosed herein for use in moderate-complexity communities and in spatially-structured systems.

Methods of the present invention provide the entire set of all probe-responsive regulators and their binding sites; it is possible that multiple regulatory proteins and binding sites will be identified for a single organism in the community. In the event that multiple regulators are identified for an organism, the pairing between regulators and binding sites will be done empirically.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

What is claimed is:

1. A method of identifying binding sites in macromolecules using small molecule mimics of naturally occurring molecules comprising:
   a. providing a reactive probe that mimics small molecule cofactors; and
   b. irreversibly binding a target macromolecule to the probe to selectively pull down or precipitate probe-bound macromolecules that comprise target nucleic acids, wherein both captured and uncaptured macromolecule fragments are sequenced in parallel to detect which fragments are enriched or depleted.

2. The method of claim 1 wherein the macromolecules include at least one of the following: DNA, RNA.

3. The method of claim 1 wherein the probe includes a photo-crosslinker, and an alkyne or an azide.

4. The method of claim 3 wherein the photo-crosslinker is diazirine or benzophenone.

5. The method of claim 4 further comprising exposing the photo-crosslinker to UV light wherein the target macromolecule interacting with the probe is covalently attached to the probe, forming a probe-bound macromolecular complex.

6. The method of claim 5 wherein the cross-linking of the macromolecular complex to the target macromolecule is performed using aldehyde, formaldehyde, or paraformaldehyde.

7. The method of claim 6 further comprising enriching the probe-bound macromolecule complex by adding an enrichment group and a detection group to the alkyne or azide portion of the probe using copper (I) cycloaddition.

8. The method of claim 6 further comprising performing click chemistry on azide or alkyne-coated beads.

9. The method of claim 7 wherein the enrichment group is biotin or avidin, and the detection group is at least one of the following: fluorophores, nanoparticles, and quantum dots.

10. The method of claim 7 wherein the macromolecular complex includes at least one of the following: biotin, GST tags, and HA tags.

11. The method of claim 10 wherein the macromolecular complex is removed from any unbound macromolecules by affinity purification through binding to avidin or streptavidin.

12. The method of claim 11 wherein fractions from the avidin-bound, streptavidin-bound, and/or the unbound macromolecules are harvested for sequencing.

13. The method of claim 12 wherein, post-elution, the cross-linking in the avidin-bound or streptavidin-bound fractions will be reversed by heat treatment from which fractions of the macromolecules will be separated.

14. The method of claim 5 wherein the macromolecule irreversibly binding the probe is identified by LC-MS, DNA or RNA sequencing, or both, which yields a set of macromolecules binding the probe.

* * * * *